(12) United States Patent
Kellogg

(10) Patent No.: US 6,569,170 B1
(45) Date of Patent: May 27, 2003

(54) METHOD OF CLEANING SKIN

(76) Inventor: David L. Kellogg, 17482 Luther, Irvine, CA (US) 92614

( * ) Notice: Subject to any disclaimer, the term of this patent is extended or adjusted under 35 U.S.C. 154(b) by 0 days.

(21) Appl. No.: 09/957,518

(22) Filed: Sep. 20, 2001

(51) Int. Cl.⁷ .............................................. A61B 17/50
(52) U.S. Cl. ............................ 606/131; 601/2; 15/22.1; 422/20
(58) Field of Search .............................. 606/131; 601/2; 422/20; 15/22.1, 22.2

(56) References Cited

U.S. PATENT DOCUMENTS

| | | | |
|---|---|---|---|
| 2,970,073 A | * | 1/1961 | Prange |
| 3,166,772 A | * | 1/1965 | Bodine, Jr. |
| 3,375,820 A | * | 4/1968 | Kuris et al. |
| 3,409,925 A | * | 11/1968 | Bodine, Jr. |
| 3,481,687 A | * | 12/1969 | Fishman |
| 3,699,952 A | | 10/1972 | Waters et al. |
| 3,809,977 A | * | 5/1974 | Balamuth et al. |
| 3,906,940 A | | 9/1975 | Kawada |
| 3,980,906 A | * | 9/1976 | Kuris et al. |
| 4,040,414 A | | 8/1977 | Suroff |
| D245,948 S | | 10/1977 | Wolff |
| 4,203,431 A | | 5/1980 | Abura et al. |
| 4,281,987 A | | 8/1981 | Kleesattel |
| 4,724,563 A | | 2/1988 | Fry et al. |
| 4,919,117 A | * | 4/1990 | Muchisky et al. |
| 5,012,797 A | | 5/1991 | Liang et al. |
| 5,339,804 A | * | 8/1994 | Kemp ............................ 601/2 |
| 5,546,624 A | * | 8/1996 | Bock ........................... 15/22.1 |
| 5,803,099 A | * | 9/1998 | Sakuta et al. ............. 134/56 R |
| 6,102,923 A | * | 8/2000 | Murayama .................. 606/161 |
| 6,267,305 B1 | * | 7/2001 | Kondo ..................... 239/428.5 |

FOREIGN PATENT DOCUMENTS

WO      WO 97/22325      6/1997

* cited by examiner

*Primary Examiner*—Ralph A. Lewis
(74) *Attorney, Agent, or Firm*—Eric Karich

(57) ABSTRACT

An ultrasonic cleaner has a handle having a proximal end, a distal end, a hollow interior, and an exterior gripping surface. A brush mounting point is positioned at the proximal end of the handle and an ultrasonic vibrator is positioned within the hollow interior and operably attached to the brush mounting point. A battery is operably positioned within the hollow interior of the handle for providing power to the ultrasonic vibrator. A skin cleaning brush is mounted on the brush mounting point. The invention includes a method of cleaning skin using an ultrasonic cleaner. Ultrasonic vibration is transmitted from the ultrasonic vibrator, through the brush mounting point, to a plurality of brush bristles of the skin cleaning brush, and the skin cleaning brush is used to scrub the skin. In this arrangement, the plurality of brush bristles effectively transmit the ultrasonic vibration to the skin and work in conjunction with the liquid cleaning solvent to clean the skin.

3 Claims, 1 Drawing Sheet

METHOD OF CLEANING SKIN

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

This invention relates generally to methods for cleaning skin, and more particularly to a method for using an ultrasonic cleaner for cleaning the skin.

2. Description of Related Art

Cleaning mechanisms that use ultrasonic vibrations to increase their cleaning effectiveness are known in the art, especially in the field of leaning teeth. An example of such a cleaner is shown in Kleesattell, U.S. Pat. No. 4,281,987, which teaches an ultrasonically driven dental prophylaxis unit.

Ultrasonics are also used for various methods of treating skin. Examples of such uses are shown in the following:

Liang et al., U.S. Pat. No. 5,012,797, teaches a method for removing wrinkles using an ultrasonic surgical tool that is adapted to abrade soft tissue.

Bock, WO 97/22325, teaches a method of using sonic and ultrasonic vibrations to increase the uptake of therapeutic agents through the skin.

Suroff, U.S. Pat. No. 4,040,414, teaches an ultrasonic personal care instrument with a suction device for sucking blockages out of pores to remove blackheads.

Aside from such instruments, ultrasonic devices have typically not been used on the skin, and have never been used for cleaning the skin. Instead, skin cleaning devices have been restricted to rotary motor cleaners that are well documented in the art. Examples of this design include Abura et al., U.S. Pat. No. 4,203,431 (facial treatment device), Wolff, U.S. Pat. No. Des. 245,948 (facial cleaning apparatus), Kawada, U.S. Pat. No. 3,906,940 (facial treatment device with oscillating rotary massaging member), Waters et al., U.S. Pat. No. 3,699,952 and Fry et a., U.S. Pat. No. 4,724,563 (skin treating appliance with orbitally driven brush).

The prior art teaches ultrasonic cleaners for cleaning teeth; the prior art teaches cleaning skin with an orbitally driven brush; and the prior art teaches the use of ultrasonics for abrading the skin for removing wrinkles. However, the prior art does not teach a method for using an ultrasonic brush to clean the skin. The present invention fulfills these needs and provides further related advantages as described in the following summary.

SUMMARY OF THE INVENTION

The present invention teaches certain benefits in construction and use which give rise to the objectives described below.

The present invention provides a method of cleaning skin using an ultrasonic cleaner. The ultrasonic cleaner has a handle having a proximal end, a distal end, a hollow interior, and an exterior gripping surface. A brush mounting point is positioned at the proximal end of the handle and an ultrasonic vibrator is positioned within the hollow interior and operably attached to the brush mounting point. A means for providing power to the ultrasonic vibrator is included and a skin cleaning brush is mounted on the brush mounting point. In use, ultrasonic vibration is initiated in the ultrasonic vibrator, the ultrasonic vibration being transmitted through the brush mounting point to a plurality of brush bristles of the skin cleaning brush; and the skin cleaning brush is used to scrub the skin. In this arrangement, the plurality of brush bristles effectively transmit the ultrasonic vibration to the skin and work in conjunction with the liquid cleaning solvent to clean the skin.

A primary objective of the present invention is to provide a method for cleaning the skin using an ultrasonic cleaner, the method having advantages not taught by the prior art.

Another objective is to provide a cleaning method that removes blockages to remove and prevent blackheads, acne, and other skin blemishes.

A further objective is to provide an ultrasonic cleaner adapted for cleaning the skin, the ultrasonic cleaner functioning to thoroughly clean the skin without damaging the skin.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings.

DETAILED DESCRIPTION OF THE INVENTION

Figure 1:
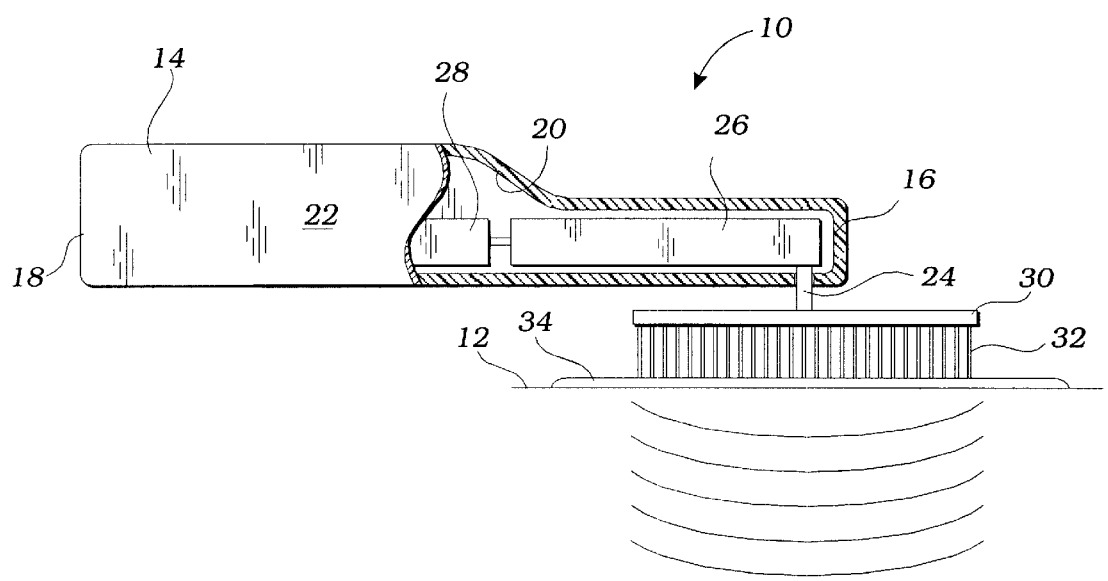
FIG. 1 is a perspective view of the preferred embodiment of the present invention.

The above-described drawing figures illustrate the invention, a method of cleaning skin 12 using an ultrasonic cleaner 10 that transmits ultrasonic vibrations into the skin 12 through a plurality of brush bristles 32 that operate in conjunction with a liquid cleaning solvent 34 to effectively clean the skin 12 and remove blackheads and other blockages of the pores.

As shown in FIG. 1, the ultrasonic cleaner 10 includes a handle 14 having a proximal end 16, a distal end 18, a hollow interior 20, and an exterior gripping surface 22. The handle 14 is preferably a rigid, elongate molded plastic housing; however, a softer and more resilient ball shape could also be used, or a rigid metal housing, or any other equivalent material or shape that can be devised by those skilled in the art. A rubberized coating could also be added to the exterior gripping surface 22 to facilitate gripping the ultrasonic cleaner 10 if it gets wet during use, although this feature is not required.

A brush mounting point 24 is positioned at the proximal end 16 of the handle 14. An ultrasonic vibrator 26 is positioned within the hollow interior 20 and operably attached to the brush mounting point 24. The ultrasonic vibrator 26 is preferably an eccentrically weighted motor, well known in the prior art, although any means for generating an ultrasonic vibration can be used. For purposes of this application, ultrasonic refers to vibrations in the range of approximately 1,000 to 1,000,000 cycles per second.

The ultrasonic vibrator 26 is preferably operable attached directly to the brush mounting point 24. In an alternative embodiment, however, the ultrasonic vibrator 26 is firmly attached to the housing, which forms the brush mounting point 24 at the proximal end 16 such that vibrations from the ultrasonic vibrator 26 are transmitted to the proximal end 16 through the housing.

A means for providing power to the ultrasonic vibrator 26 is included, preferably a battery 28 positioned within the hollow interior 20 and electronically connected to the ultrasonic vibrator 26. In an alternative embodiment, the means for providing power is a power cord So (not shown) adapted to be connected to an external power outlet. Since the power source is not an important feature of the device, any practical method of powering the ultrasonic vibrator 26 should be considered within the scope of the present invention, and the matter is not described in any greater detail herein.

While the ultrasonic vibrator 26 is shown positioned inside an inner chamber of the handle 14, the hollow interior 20 does not necessarily have to be constructed in this manner. The hollow interior 20 is only required to be a shaped portion that functions to contain or mount the ultrasonic vibrator 26; however, in the preferred embodiment, the hollow interior 20 is a watertight compartment so that the ultrasonic vibrator 26 and the battery 28 are protected from water during the use of the ultrasonic cleaner 10.

A skin cleaning brush 30 is mounted, or mountable, on the brush mounting point 24. The skin cleaning brush 30 has a plurality of brush bristles 32. The plurality of brush bristles 32 are critical to the effective function of the invention. Previously, the use of bristles has been restricted to cleaning teeth. It is important that the plurality of brush bristles 32 be rigid enough to effectively transmit the ultrasonic vibrations, yet soft enough to not irritate or damage the skin 12 during use. Following the teachings provided herein, those skilled in the art can select the grade and thickness of the plurality of brush bristles 32 such that they are as soft as possible while still remaining effective. A properly selected plurality of brush bristles 32 is, however, surprisingly effective in cleaning the skin 12.

In use, a liquid cleaning solvent 34 is used to coat the skin 12. The liquid cleaning solvent 34 is preferably a combination of water and soap, preferably DIAL® due to its antibacterial properties, although any soap, detergent, similar material or solution can be used. In addition to a soap, it is also helpful to include an astringent to tighten the pores following use of the ultrasonic cleaner 10.

While we refer specifically to coating the skin 12 with the liquid cleaning solvent 34, it is equivalent to add the liquid cleaning solvent 34 to the plurality of brush bristles 32 and then use the ultrasonic cleaner 10 to clean the skin 12. Similarly, water can be splashed onto the skin 12, a concentrated soap can be added to the plurality of brush bristles 32, and then used to clean the skin 12. It is also possible to clean using just water, which itself acts as a solvent; however, this is not preferred because the addition of a soap or detergent is much more effective in cleaning and removing the grease and oil that tends to clog the skin 12. The specific method of applying the water and the soap is not important, only that the liquid cleaning solvent 34 be available to clean the skin 12, as described below.

Ultrasonic vibration is then initiated in the ultrasonic vibrator 26, the ultrasonic vibration being transmitted through the brush mounting point 24 to the plurality of brush bristles 32 of the skin cleaning brush 30; and the skin cleaning brush 30 is used to scrub the skin 12. In this arrangement, the plurality of brush bristles 32 effectively transmit the ultrasonic vibration to the skin 12 and work in conjunction with the liquid cleaning solvent 34 to clean the skin 12.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A method of cleaning skin using an ultrasonic cleaner, the method comprising the steps of:

a) providing an ultrasonic cleaner comprising
        a handle having a proximal end, a distal end, a hollow interior, and an exterior gripping surface;
        a brush mounting point positioned at the proximal end of the handle;
        an ultrasonic vibrator positioned within the hollow interior and operably attached to the brush mounting point;
        a means for providing power to the ultrasonic vibrator; and
        a skin cleaning brush mounted on the brush mounting point, the skin cleaning brush having a plurality of brush bristles;
    b) providing a liquid cleaning solvent;
    c) coating the skin with the liquid cleaning solvent;
    d) initiating ultrasonic vibration of the ultrasonic vibrator, the ultrasonic vibration being transmitted through the brush mounting point to the plurality of brush bristles of the skin cleaning brush; and
    e) scrubbing the skin with the skin cleaning brush, the plurality of brush bristles effectively transmitting the ultrasonic vibration to the skin and working in conjunction with the liquid cleaning solvent to clean the skin.

2. The method of claim 1 wherein the liquid cleaning solvent includes water and a soap.

3. The method of claim 2 wherein the liquid cleaning solvent further includes an astringent.

\* \* \* \* \*